(12) United States Patent  
Russomano et al.

(10) Patent No.: US 8,443,544 B2  
(45) Date of Patent: May 21, 2013

(54) PROCESS OF GROWING PLANTS UNDER HYPERGRAVITY CONDITIONS

(75) Inventors: Thais Russomano, Porto Alegre (BR); Felipe Prehn Falcão, Porto Alegre (BR); Marlise Araújo Dos Santos, Porto Alegre (BR); Leandro Vieira Astarita, Porto Alegre (BR); Clarice Azevedo Machado, Porto Alegre (BR); Priscila Collin, Porto Alegre (BR); Amanda Assunção Vieira, Porto Alegre (BR)

(73) Assignee: Uniao Brasileira de Educacao e Assistencia-Mantenedora da Pucrs, Porto Alegra (BR)

( * ) Notice: Subject to any disclaimer, the term of this patent is extended or adjusted under 35 U.S.C. 154(b) by 306 days.

(21) Appl. No.: 12/668,208

(22) PCT Filed: Jul. 9, 2008

(86) PCT No.: PCT/BR2008/000199  
§ 371 (c)(1), (2), (4) Date: Jan. 8, 2010

(87) PCT Pub. No.: WO2009/006719  
PCT Pub. Date: Jan. 15, 2009

(65) Prior Publication Data  
US 2010/0180499 A1    Jul. 22, 2010

(30) Foreign Application Priority Data

Jul. 9, 2007  (BR) .................................... 0705245

(51) Int. Cl.  
*A01G 1/00*  (2006.01)

(52) U.S. Cl.  
USPC ..................................................... 47/58.1 R

(58) Field of Classification Search  
USPC ..................................................... 47/58.1 R  
See application file for complete search history.

(56) References Cited

PUBLICATIONS

Fitzelle et al, Restoration of gravitropic sensitivity in starch-deficient mutans of *Arabidopsis* by hypergravity, Feb. 2001, Jornal of Experimental Botnay, VI 52, No. 355, pp. 265-275.*

Soga et al, Graviperception in growth inhibition of plant shoots under hypergravity conditions produced by centrifugation is independent of that in gravitopism and my involve mechanoreceptors, Nov. 28, 2003.*

* cited by examiner

*Primary Examiner* — Kristen C Hayes  
(74) *Attorney, Agent, or Firm* — Laurence P. Colton; Smith Risley Tempel Santos LLC

(57) ABSTRACT

A process for the germination and/or modulation of plant development by subjecting plants to simulated hypergravity conditions as a way of increasing efficiency and speed of plant development and/or germination.

5 Claims, 3 Drawing Sheets

1A

1B

PROCESS OF GROWING PLANTS UNDER HYPERGRAVITY CONDITIONS

FIELD OF THE INVENTION

The present invention relates to simulated hypergravity-like or simulated hypergravity conditions in plant development modulation. More precisely, the present invention provides apparatus and process to induce the effects caused by the increase in gravity, being applied in the modulation of germination and/or post-germinative development of different species, for example, *Eruca sativa* MiIII. The process of the invention provides several advantages, such as the increase in germination rate, fast and efficient development, high growth rate (volume and mass) and high rate of secondary metabolite production in comparison to growing processes under Earth's gravitational force (1G).

BACKGROUND OF THE INVENTION

Biological studies in space environment have increasingly received special attention from researchers. There are scientific reports showing that changes in gravity as well as changes in the activity of Earth's magnetic field may interfere in living organism development. Hypergravity is one of these changes and can be defined as the increase of weight caused by either the enhancement of the mass of a given body or the acceleration of it (simulated hypergravity condition). It can be seen during launch and re-entry of a spacecraft in the Earth's atmosphere.

On Earth, gravity is present during plant evolution, being used by them to regulate their growth and development (Soga, 2004). Nowadays, two hypotheses try to explain the mechanism of gravity perception in plants. Starch-statolith hypothesis states that dense bodies of starch called amyloplasts, found in root cells, act as a gravity sensor for plants (Kiss et al, 1996; Kiss et al., 1998; Fitzelle, 2001; Aubay-Centis, 2003; Kiss et al., 1999). On the other hand, protoplast pressure hypothesis, by observing genetically modified plants with few amyloplasts, asserts that gravity perception is caused by the weight of root cell content (Caspar, 1989; Guisinger, 1999; MacCleery and Kiss, 1999 Soga et al., 2004; Soga et al., 2005). However, until now, most data referring to gravity influence in plant physiology and morphology have been obtained from plants subject to changes in gravitational vector orientation (Aubay-Centis, 2003). For this purpose, experiments in space provide microgravity conditions, while experiments based on centrifuges provide hypergravity simulated conditions (Soga, 1999).

Experiments under simulated hypergravity can represent the mechanisms involved in animals or plants, in tissues or cells in response to the increase in the gravitational force (van Loon et al., 1993). In the same way, it is possible to create on Earth, by using human centrifuges, a hypergravity environment similar to those generally found in space missions or during an abrupt maneuver of a high performance aircraft. In plants, hypergravity produced by centrifugation is used to analyze the responses of plant seeding to gravity stimulus (Hoson, 2002), although this technique has been employed in the separation of cell components, but only as a primary stimulus (Russomano et al., 2007). Gravitational forces greater than 1G have been useful for studying gravity role in plant growth (Kasahara et al., 1995). Experiments carried out by Hoson (2002) showed that hypergravity produced by centrifugation increased cell wall stiffness due to gravitational force resistance (Soga et al., 1999; Soga, 2004; Hoson et al., 2002). In the same way, it was noticed growth inhibition of elongation in mustard epicotyles (Waitron and Brett, 1990), radish and cucumber hypocotyles (Kasahara et al., 1990), cress hypocotyles (Hoson et al, 1996), azuki bean hypocotyles (Soga et al., 1999), corn coleoptiles and mesocotyls (Soga et al, 2003) and *A. thaliana* inflorescence stems (Tamaoki et al., 2006) in response to hypergravity. These results suggest that growth inhibition is due to the reduction of cell wall mechanical extensibility (Soga et al., 1999; Hoson et al., 2002; Soga et al., 2003; Soga et al., 2004).

However, morphological experiments carried out by the present inventors showed that arugula seeds germinate faster when exposed to simulated hypergravity. Such results are amazing considering the State of the Art and constitute the starting point to the present invention development.

Scientific and patent literatures regarding publications that are only partially related to the subject of the present invention, however, do not anticipate or suggest, even indirectly, any of the objects of the present invention.

The article entitled "Simulated microgravity and hypergravity attenuate heart tissue development in explant culture" reports the study about hypergravity influence on heart tissue morphogenesis.

U.S. Pat. No. 6,008,009, owned by Universities Research Association and entitled "Centrifuge-operated specimen staining method and apparatus" describes a method and an apparatus of preselected staining where the liquid stained reagents are applied and removed from the staining chamber.

International patent application WO 00/30718, filed by Arthur Kreitenberg and entitled "Exercise apparatus involving centrifugal forces", describes an exercise apparatus involving centrifugal forces where centrifugal acceleration and Earth gravitational acceleration are summed.

European document EP1030554, owned by Oceaneering International, Inc. and entitled "Method and apparatus for cytoplasmic loading using an impact-mediated procedure" describes a method and an apparatus for the introduction of macromolecules into the cytoplasm of living cells by an impact-mediated procedure that compresses cells with a predetermined number of solid particles in a blast of propellant gas. This procedure can be changed by gravitational conditions and is preferably carried out under hypergravity conditions.

U.S. Pat. No. 3,882,634, by NASA, describes a rotary plant growth accelerating apparatus based on rotation and translation motions about horizontal axes in order to administer nutrients to plants during rotation. Horizontal planetary path reduces gravity effects, that is, it simulates microgravity effects, accelerating plant growth.

U.S. Pat. No. 3,911,619, by Gravi-Mechanics Co., describes an apparatus for seed sprouting also based on rotation motions about horizontal axes. Horizontal planetary path reduces gravity effects, accelerating seed sprouting, and avoiding problems associated to gravity.

U.S. Pat. No. 3,973,353, by Gravi-Mechanics Co., describes a different apparatus to accelerate plant growth based on the application of rotation and translation motions about horizontal axes in order to administer nutrients to plants during rotation. Horizontal planetary path reduces gravity effects, accelerating plant growth.

Results obtained by the present invention system and process are amazing from scientific and patent literature point of view.

SUMMARY OF THE INVENTION

It is an objective of the present invention to provide a process of plant growth and development under simulated hypergravity conditions. Therefore, the invention consists of an apparatus and a process that simulate the exposure to a hypergravity environment, which increases plant germination and/or post-germinative development.

Another objective of the present invention is to provide a process for large-scale plant growth in a system that supplies hypergravity simulated environment.

Yet another objective of the present invention is to provide a process for large-scale plant growth that presents accelerated cell growth and cell differentiation.

Another objective of the present invention is a process for large-scale plant growth, which has a significantly greater growth (volume and mass) and a faster differentiation rate for an equal period in comparison to others under Earth's gravity.

These and other objectives of the present invention should be evident and valued from the detailed description of the invention.

DETAILED DESCRIPTION OF THE INVENTION

From the detailed description of the present invention, those professionals familiar with the subject will immediately identify its great technical and economic value. For the purposes of the present invention, the term "hypergravity" is defined as that resulting from conditions capable of inducing the effects caused by the increase in the gravitational force, using hypergravity-like or simulated hypergravity situations (in this case, rotation). The examples described below aim to provide ways of reproducing the invention, but they should not be interpreted as a limitation to the invention nor the only way of accomplishing it.

Example 1

A plastic pot with a diameter of 60 mm and height of 62 mm, with 44 g of dark soil (Mumosoto, a kind of humus) and 10 seeds of *Eruca sativa* Mill, (KAD type, with increased moisture) was put in each arm end of a centrifuge, adjusted to rotate at 92 rpm, in order to provide a $+7G_z$ environment. Seeds mentioned above were subjected to this condition during intermittent periods—in this case from 8 AM to 5 PM, totaling 9 h/day for four consecutive days. At night, hypergravity action was removed, that is, from 5 PM to 8 AM next day plants remained under Earth's gravity force (1G). Pots were closed with a plastic coverage to avoid water evaporation by forced convection resulting from the spinning. Pots were safely fixed to the arm ends of the centrifuge with a metal bolt. Thus, during rest the pot opening remained at a 90° angle to the centrifuge arm. During centrifuge rotation, the pot remained at 0° angle to the centrifuge arm, simulating an increase of Earth's gravitational force in the z axis. A 3-millimeter hole was made on the side of each pot to allow ventilation. Two similar plastic pots were kept open in the same room to be used as control (1G). Room temperature was adjusted to 22° C., and water (0.5 mL volume) was added to the pots before and immediately after the experiment. Experiment was carried out twice in order to verify the reproducibility of it.

Figure 1:
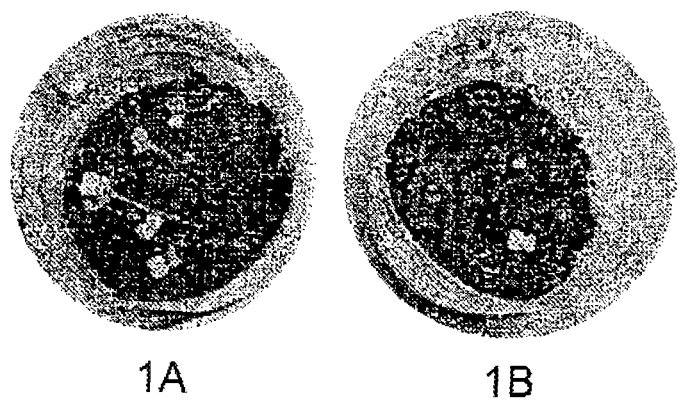
FIG. 1 shows individual development of *Eruca sativa* Mill subject to two different environments, a simulated hypergravity environment ($+7G_z$—FIG. 1A) and Earth's gravity environment (1G—FIG. 1B), used as control. Tests were carried out during an intermittent period of four days.

Results showed that the seeds exposed to $+7G_z$ germinated in three days in comparison to the four days necessary for the seeds in the control pots. At the end of the process, plants subject to simulated hypergravity were removed and measured by a caliper rule from root to top. Two embodiments of the invention process were:

(i) in the first embodiment, the mean height of the plants subject to $+7G_z$ was 3.2 cm, against a mean of 1.9 cm of control plants, showed in FIG. 1;

(ii) in the second embodiment, when more plants were subjected to the invention process (n=14), the mean height of the plants subjected to simulated $+7G_z$ was 2.2 cm, a significantly greater value than the development of plants under 1G (control), which was 1.8 cm (p=0.02). Results described above support the applicability of the present invention process in the modulation of plant germination and/or growth.

Although the technical reasons for such amazing results are not totally elucidated, some guidelines to technical debate could explain such results. One of them could be related to the influence of plant hormone auxin, which modulates plant growth. Term auxin comes from Greek "auxein", that means to grow; therefore, auxin is characterized by being able to induce cell elongation in stem sub-apical region. Auxin is a vegetal hormone responsible for plant cell growth, stem and root elongation, and fruit development. It is well known that auxins control gravitropism, promote apical dominance, and retard abscission. Auxin also affects physiologic processes, including phototropism, gravitropism, fruit development, among other functions. However, elongation is one of the most important effects of auxin action. One important stage of elongation is cell edge acidification caused by an electrochemical gradient, which leads to proton secretion through plasmatic membrane, promoting cell wall acidification, resulting in enzymatic activity increase. This enzymatic activity increase promotes cell structure ductility, enabling cell elongation. When water penetrates cell, osmotic pressure forces expand it. The amazing and significant development of *Eruca sativa* Mill after four days of exposition to intermittent simulated hypergravity could therefore derive from the variation of the amount of auxin. Likewise, hypergravity may change auxin levels in tissues. If so, it can be deduced that changes in the components of secondary metabolism may happen, such as enzymatic activities of phenylpropanoid and terpenoid pathway, as well as in the synthesis of development regulatory molecules.

Example 2

Figure 2:
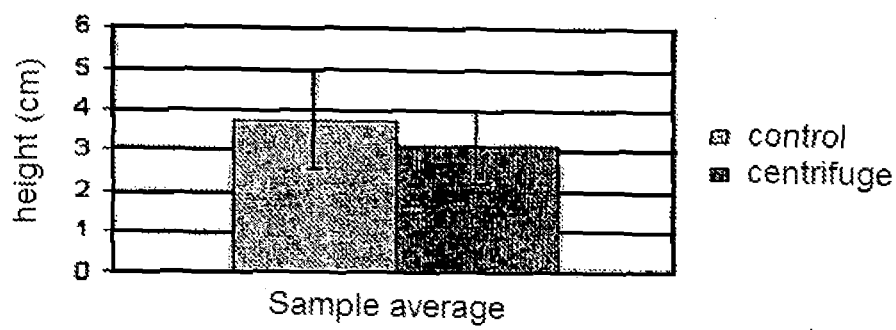
FIG. 2 shows the comparison of arugula growth in soil method.
Figure 3:
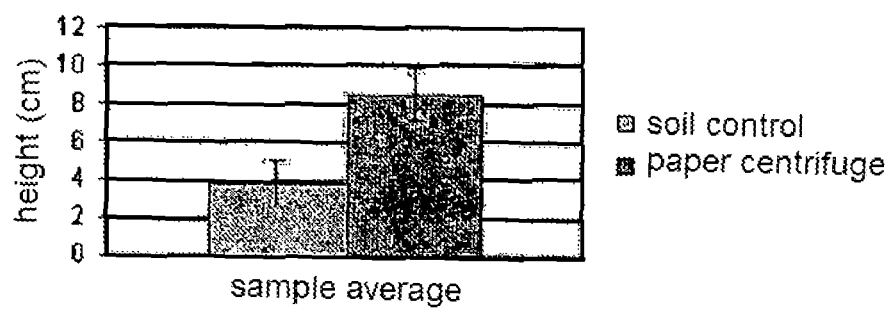
FIG. 3 shows the difference between the growths obtained in paper with water-centrifuge and soil-control.

From the results obtained in Example 1, new experiments were carried out. In the present example, only soil method was employed, despite the variances obtained from the water factor. At the end of this experiment, however, it was visually noticed that the soil of the samples in the centrifuge was dry on the surface, possibly negatively influencing plant growth. Difficulty in establishing the exact amount of water that should be used to have the same moisture under 1Gz as well as under $+7G_z$ was evident. FIG. 2 shows that control sample growth (3.76±1.21) was statistically greater (p=0.00) than centrifuge sample growth (3.15±1.00). However, when comparing growths in paper with water-centrifuge of Example 1 experiments (8.44±1.43) to soil-control (3.76±1.21), a significant difference (p=0.00) was noticed, as showen in FIG. 3. Therefore, the last experiment aimed only at the application of paper with water method in order that the water factor did not interfere in results.

The water in paper method described herein is for seeds cultivated on paper, commonly called germination paper, namely, papers moistened with water. Germination papers of present invention are preferably rectangular papers (18 cm×6 cm) having around 15 seeds over each paper. Each 300 ml empty container held three papers, in a way that each container comprised 45 seeds. Then, 80 ml of water was added to each container, and the containers were covered with a plastic covering having small holes therethrough (5 mm), in order to minimize water evaporation. Examples of other uses of such a water in paper method can be found in the literature, such as Mian, M. A. R. and Nafziger, E. D., Seed size and water potential effects on germination and seedling growth of winter wheat, Vol. 34 (1), 169-171 (1994); Pederson, G. A., White clover seed germination in agar containing tall fescure leaf extracts Vol. 26 (6), 1248-1249 (1986); and Dutt, D., Lal, M., Malik, R. S., and Upadhyay, M. K., Development of specialty papers is an art: Seed germination paper from indigenous raw materials Journal of Scientific & Industrial Research (64), 440-442 (2005).

In the following experiment it was obtained a greater growth in centrifuge samples (4.00±1.01) with statistically significant values (p=0.00). However, plants did not reach 1 cm of difference from control (3.49±1.27). In both samples, less growth was noticed, because mean height did not exceed 4.5 cm, which differs from previous experiments, when mean height was up to 8.5 cm. Factors that could have influenced results were low temperature and moisture conditions.

In the present invention, total phenolic compounds were quantified in both conditions and were not significantly different (p=0.06), showing, therefore, that the hypergravity simulation did not affect the phenol production in plants (Table 2).

TABLE 2

| Values of total phenols in gallic acid equivalents (mg/g) | |
|---|---|
| Control | Centrifuge |
| 0.08538 | 0.08850 |
| 0.06914 | 0.07852 |
| 0.05898 | 0.08928 |
| 0.06152 | 0.07912 |
| 0.07970 | 0.07872 |
| 0.06758 | 0.07952 |

TABLE 2-continued

| Values of total phenols in gallic acid equivalents (mg/g) | |
|---|---|
| Control | Centrifuge |
| 0.05172 | 0.07150 |
| 0.08830 | 0.07932 |

Figure 4:
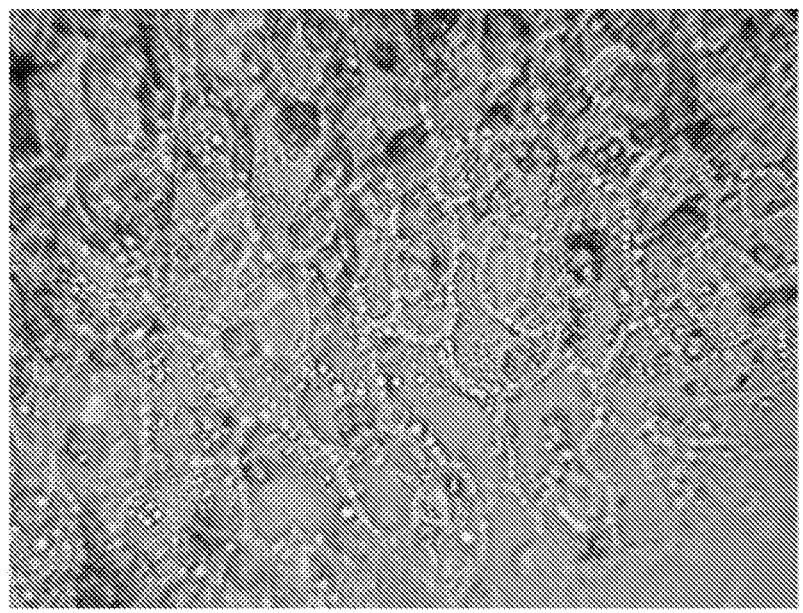
FIG. 4 shows a histological cut of a plant subject to simulated hypergravity.
Figure 5:
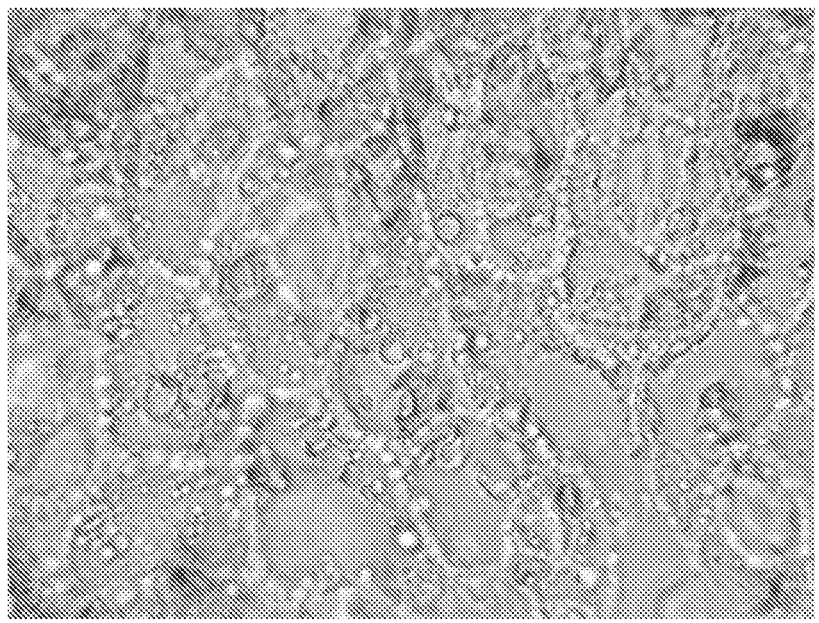
FIG. 5 shows another histological cut of a plant subject to simulated hypergravity.
Figure 6:
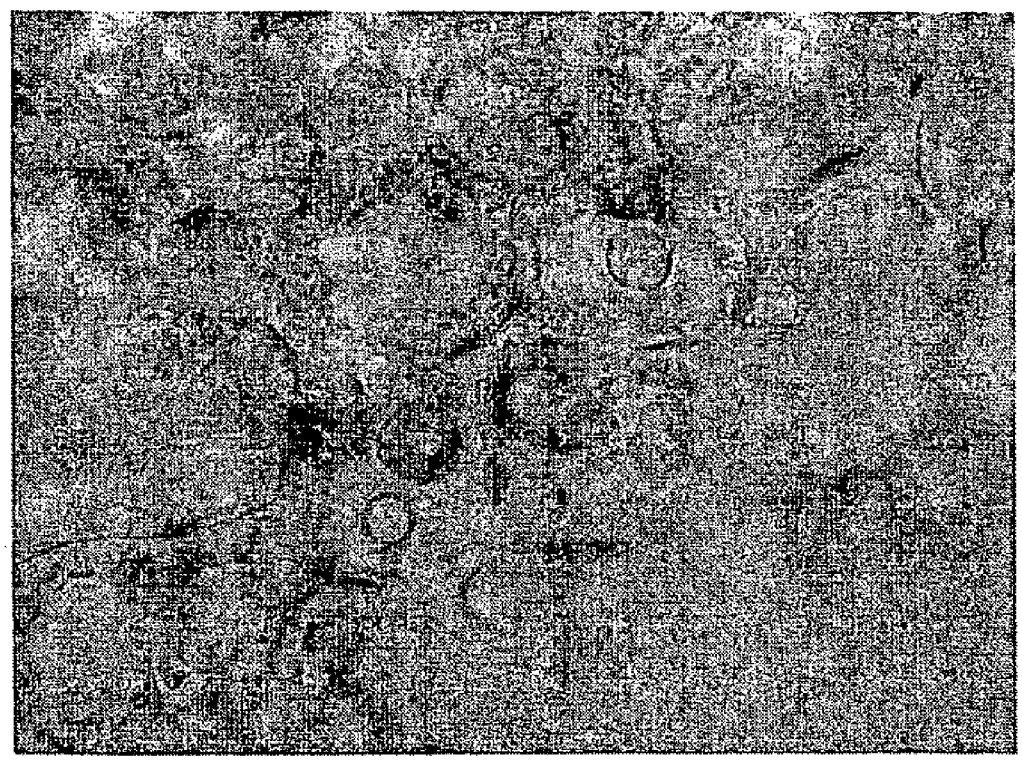
FIG. 6 shows a histological cut of a plant not subject to simulated hypergravity (control).

Finally, in the histological cut of arugula cotyledons a difference in its essential oil distribution was noticed. In cotyledon-centrifuge cell, oil was distributed in the whole cell membrane, and small oil drops spread in cytoplasm were noticed (FIGS. 4 and 5). On the other hand, in cotyledon-control cells, oil was located in the center of the cell, showing a single, big drop (FIG. 6).

By means of preliminary studies carried out at Microgravity Center—Pontifical Catholic University of Rio Grande do Sul, it was concluded that *Eruca sativa* seed germination and growth are greater when these seeds are under intermittent simulated hypergravity conditions.

Results presented suggest that plant growth and/or development under simulated hypergravity can be an alternative to minimize one of the main problems confronted by agribusiness and pharmaceutical and cosmetic industry. In a shorter period and with low operational costs, it is possible to have an increase of vegetal raw production, as well as to provide quantitatively standardized vegetal extracts. In the invention process, simulated hypergravity level, duration of exposure and/or intervals are chosen according to the intended result of plant growth/development.

Those professionals familiarized with plant growth and/or germination will immediately value achievements and identify several technical, economic, environmental and health advantages of the technology here described. Small variations in the way of carrying out the invention here described should be considered within the scope and spirit of this invention and its claims.

The invention claimed is:

1. A process for growing plants, comprising at least one step of submitting vegetal material of the plants to hypergravity conditions, resulting in a modification of the development of said plants, which step comprises the simulation of hypergravity during intermittent periods, wherein each of the intermittent periods is about 9 hours.

2. The process according to claim 1, wherein said hypergravity condition is simulated using a centrifuge rotating at 92 revolutions per minute.

3. The process according to claim 1, wherein the vegetal material is seeds of the *Eruca sativa* plant.

4. The process according to claim 1, wherein the vegetal material is previously germinated plants of the *Eruca sativa* plant.

5. The process according to claim 1, wherein the hypergravity is at least 7G.

* * * * *